United States Patent [19]

Cohen et al.

[11] 4,179,568
[45] Dec. 18, 1979

[54] (N-LOWER ALKYL-3,5-DIOXO-3-PYRROLIDINYL)THI-OALKANOYLPYRROLIDINE-AND PIPERIDINE-CARBOXYLIC ACID COMPOUNDS

[75] Inventors: Allen I. Cohen, Highland Park; Kishin J. Kripalani, East Brunswick, both of N.J.

[73] Assignee: E. R. Squibb & Sons, Inc., Princeton, N.J.

[21] Appl. No.: 929,877

[22] Filed: Jul. 31, 1978

[51] Int. Cl.² .................. C07D 401/12; C07D 403/12; A61K 31/445; A61K 31/40
[52] U.S. Cl. ................... 546/208; 260/326.25; 424/1; 424/267; 424/274
[58] Field of Search ............... 260/326.25; 546/208; 424/1

[56] References Cited

U.S. PATENT DOCUMENTS

| | | | |
|---|---|---|---|
| 4,046,889 | 9/1977 | Ondetti et al. | 260/326.2 |
| 4,086,338 | 4/1978 | Cushman et al. | 424/274 |
| 4,091,024 | 5/1978 | Ondetti et al. | 260/326.25 |
| 4,105,776 | 8/1978 | Ondetti et al. | 260/326.25 |
| 4,116,962 | 9/1978 | Ondetti et al. | 260/326.25 |
| 4,129,571 | 12/1978 | Ondetti et al. | 260/326.25 |

OTHER PUBLICATIONS

The Chemistry of the Thio Group; pp. 271, 272, 294, 295, 296, 297, 318, 319 (1974).

*Primary Examiner*—Donald G. Daus
*Assistant Examiner*—Mary C. Lee
*Attorney, Agent, or Firm*—Lawrence S. Levinson; Donald J. Barrack

[57] ABSTRACT

Compounds having the formula

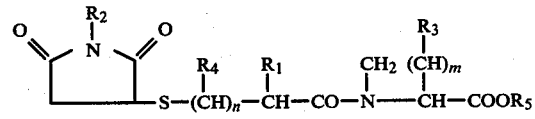

wherein $R_1$ and $R_4$ each is hydrogen, lower alkyl or phenyl-lower alkyl; $R_2$ is lower alkyl; $R_3$ is hydrogen, hydroxy or lower alkyl; $R_5$ is hydrogen or lower alkyl; m is 2 or 3; and n is 0, 1 or 2; are useful analytical tools.

7 Claims, No Drawings

(N-LOWER ALKYL-3,5-DIOXO-3-PYRROLIDINYL)THIOALKANOYLPYRROLIDINE-AND PIPERIDINE-CARBOXYLIC ACID COMPOUNDS

BACKGROUND OF THE INVENTION

U.S. Pat. No. 4,046,889, issued Sept. 6, 1977 describes a group of thioalkanoyl derivatives of azetidine-, pyrrolidine- and piperidinecarboxylic acid derivatives which are useful as inhibitors of the conversion of the decapeptide angiotensin I to angiotensin II, and are therefore useful in reducing or relieving angiotensin related hypertension.

Among the compounds described in the abovementioned patent are those having the structural formula

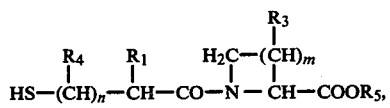

and salts thereof, wherein the variables are as defined hereinafter. These compounds readily convert to the corresponding dimers (through the sulfur atom) and other more polar products in biological fluids such as blood and urine. This conversion presents a problem in running studies to follow the time course of the compounds in the bodies of animals or man.

It is an object of this invention to prevent or minimize the conversion of the compounds illustrated above immediately upon the collection of biological samples containing these compounds, and thus allow for the collection of reliable analytical data.

These and other objectives may be realized by using the method and novel compounds described hereinafter.

SUMMARY OF THE INVENTION

Compounds having the formula

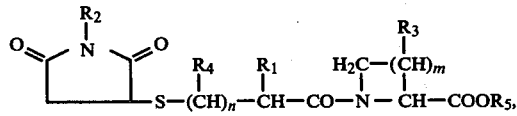

and salts thereof, are useful analytical tools. In formula I, and throughout the specification, the symbols are as defined below.

$R_1$ and $R_4$ each is hydrogen, lower alkyl or phenyl-lower alkyl;
$R_2$ is lower alkyl (ethyl is preferred);
$R_3$ is hydrogen, hydroxy or lower alkyl;
$R_5$ is hydrogen or lower alkyl;
m is 2 or 3; and
n is 0, 1 or 2.

The expression "lower alkyl", as used throughout the specification, includes straight and branched chain hydrocarbon radicals from methyl to heptyl, e.g., methyl, ethyl, propyl, isopropyl, butyl, isobutyl, t-butyl, pentyl, isopentyl and the like. Those lower alkyl groups having 1 to 4 carbon atoms, especially those having 1 to 2 carbon atoms are preferred. The preferred phenyl-lower alkyl group is phenylmethyl.

The method of this invention comprises the stabilization of a compound having the formula

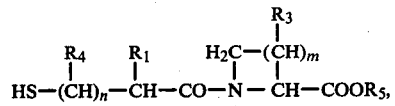

or a salt thereof, in a biological fluid by the addition to the biological fluid of a maleimide derivative having the formula

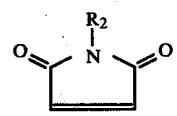

in an amount sufficient to react with all of the compound of formula II.

DETAILED DESCRIPTION OF THE INVENTION

In the development and use of a compound of formula II as a hypotensive agent, various studies are required to show the time course of the drug in the body. These studies involve the gathering of both animal and human data. It is important to know for different time intervals after administration of the drug how much of the drug is in the blood stream, how much of the drug has been excreted from the body, how much of the drug has been metabolized, etc.

In order to insure the collection of accurate metabolism data, it is essential that conversion of the drug be prevented or minimized immediately upon the taking of a biological sample.

In accordance with the method of this invention a biological fluid such as blood or urine, believed to contain a compound of formula II, of a salt thereof, is mixed with a maleimide derivative of formula III. The compounds of formula II and III react in situ to form the product of formula I, or salt thereof, and allow for accurate time-based quantitative measurements using known analytical techniques, e.g., thin-layer chromatography, thin-layer radiochromatography, liquid chromatography or gas chromatography.

Pure samples of the compounds of formula I, and salts thereof, must also be synthesized for use as standards in the various analytical techniques. This can be accomplished by reacting a compound of formula II, or a salt thereof, with a maleimide derivative of formula III, in water. The reaction can conveniently be run at room temperature, and can be carried out in an inert atmosphere, e.g., argon or nitrogen. The reaction proceeds most readily at pH 7, and it is, therefore, desirable to add a buffer to the reaction mixture.

The starting compounds of formula II, and salts thereof, are known in the art; see, for example, U.S. Pat. No. 4,046,889 issued Sept. 6, 1977. As described therein, the compounds of formula II can be prepared by coupling an acid or ester of the formula

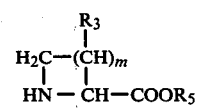

with a haloalkanoic acid of the formula

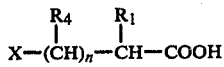

$$X-(CH)_n-CH-COOH \quad V$$

wherein X is a halogen, preferably chlorine or bromine. The coupling is accomplished by one of the known procedures in which the haloalkanoic acid is activated, prior to reaction with a compound of formula IV, involving formation of a mixed anhydride, symmetrical anhydride, acid chloride, active ester, or use of Woodward reagent K, EEDQ (N-ethoxycarbonyl-2-ethoxy-1,2-dihydroquinoline) or the like.

The product of this reaction is a compound of the formula

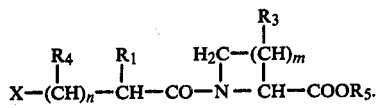

This product is subjected to a displacement reaction with the anion of a thioacid of the formula

$$Y-CO-SH, \quad VII$$

wherein Y is lower alkyl, phenyl or phenyl-lower alkyl, yielding a product of the formula

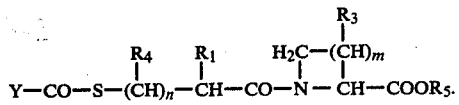

Ammonolysis of a product of formula VIII yields the starting compound of formula II.

Additional processes for the preparation of the starting compounds of formula II are described in U.S. Pat. No. 4,046,889; the disclosure of the patent is incorporated herein by reference.

The compounds of formula I exist in stereoisomeric forms or in racemic mixtures thereof. All of these are within the scope of this invention.

The studies carried out to obtain metabolism data for the compounds of formula II can be run using radioactive analogues of the compounds of formula II. For example, sulfur-35 may be substituted for the sulfur atom in the compound, tritium may be substituted for one or more of the hydrogen atoms, carbon-14 may be substituted for one or more of the carbon atoms, etc. Radioactive analogues are included within the definition of the structural formula II. In the instance wherein a radioactive compound of formula II is being stabilized, the product of formula I will be the corresponding radioactive analogue. Radioactive analogues are included within the definition of structural formula I.

The following examples are specific embodiments of this invention.

EXAMPLE 1

1-[D-3-[(1-Ethyl-2,5-dioxo-3-pyrrolidinyl)thio]-2-methyl-1-oxopropyl]-L-proline

Method 1

1-(3-Mercapto-2-methyl-1-oxopropyl)-L-proline (11.94 g) is dissolved in 220 ml of water under argon. To this is added 6.88 of N-ethylmaleimide and the reaction mixture is adjusted to pH 7 with dilute sodium hydroxide. After twenty minutes, the reaction mixture is extracted once with ethyl acetate. The aqueous layer is acidified with concentrated hydrochloric acid to pH 2, saturated with sodium chloride and extracted into ethyl acetate. The ethyl acetate extracts are dried over magnesium sulfate and concentrated, yielding 18.7 g of material. This material is purified on a 1 pound silica gel column which is eluted with benzene: acetic acid (7:3). The desired fractions are pooled, concentrated to dryness and lyophilized several times from water, yielding 10.5 g of the title compound.

| Analysis Calc'd (including .5 mole H₂O | Found: |
|---|---|
| C 51.28 | 51.56 |
| H 6.60 | 6.51 |
| N 7.79 | 7.86 |
| S 9.13 | 8.82 |

Method 2

N-Ethylmaleimide (0.75 g) and 1.0 g of 1-(3-mercapto-2-methyl-1-oxopropyl)-L-proline are dissolved in 50 ml of 0.03 M phosphate buffer, pH 7. The solution is allowed to stand at room temperature for about 1 hour. The product is isolated from the reaction mixture by adsorption on XAD-2 resin and subsequent elution with methanol. The methanol solvent is evaporated yielding 1.42 g of the title compound.

EXAMPLE 2

1-[[(1-Ethyl-2,5-dioxo-3-pyrrolidinyl)thio]acetyl]-L-proline 1-(2-Mercapto-1-oxoethyl)-L-proline (16.06 g) is taken into 340 ml of water under argon. To this, N-ethylmaleimide (10.64 g) is added, and while stirring vigorously, the pH is adjusted to 7 with dilute sodium hydroxide. After twenty minutes, the reaction mixture is extracted into ethyl acetate. The aqueous layer is acidified with concentrated hydrochloric acid to pH 2, saturated with sodium chloride and extracted into ethyl acetate. The ethyl acetate extracts are dried over magnesium sulfate and concentrated, yielding 26.4 g of material. This material is purified on a 600 g silica gel column which is eluted with benzene: acetic acid (7:3). The desired fractions are pooled concentrated to dryness in vacuo and lyophilized from water. The product is taken into water, treated with Darco G60 and relyophilized, yielding 20. g of the title compound.

| Analysis Calc'd (including .3 mole H₂O): | Found: |
|---|---|
| C 48.82 | 48.73 |
| H 5.86 | 5.64 |
| S 10.01 | 10.10 |

EXAMPLES 3-4

Following the procedure described in Example 1, but substituting the compound listed in column I for 1-(3-mercapto-2-methyl-1-oxopropyl)-L-proline, yields the compound listed in column II.

| | Column I | Column II |
|---|---|---|
| 3. | 1-(3-mercato-1-oxopropyl)-L-proline | 1-[3-[(1-ethyl-2,5-dioxo-3-pyrrolidinyl)-thio]-1-oxopropyl]-L-proline, melting point |

-continued

| | Column I | Column II |
|---|---|---|
| 4. | 1-(3-mercapto-1-oxopropyl)-2-piperidinecarboxylic acid | 129°–131° C. 1-[3-[(1-ethyl-2,5-dioxo-3-pyrrolidinyl)-thio]-1-oxopropyl]-2-piperidinecarboxylic acid, melting point of the dicyclohexylamine salt 154°–155° C. |

What is claimed is:

1. A compound having the formula

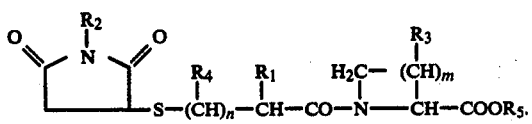

or a salt thereof, wherein $R_1$ and $R_4$ each is hydrogen, lower alkyl or phenyl-lower alkyl; $R_2$ is lower alkyl; $R_3$ is hydrogen, hydroxy or lower alkyl; $R_5$ is hydrogen or lower alkyl; m is 2 or 3; and n is 0, 1 or 2.

2. A compound in accordance with claim 1 wherein $R_5$ is hydrogen.

3. A compound in accordance with claim 1 wherein $R_2$ is ethyl.

4. The compound in accordance with claim 1, 1-[D-3-[(1-ethyl-2,5-dioxo-3-pyrrolidinyl)-thio]-2-methyl-1-oxopropyl]-L-proline.

5. The compound in accordance with claim 1, 1-[[(1-ethyl-2,5-dioxo-3-pyrrolidinyl)thio]-acetyl]-L-proline.

6. The compound in accordance with claim 1, 1-[3-[(1-ethyl-2,5-dioxo-3-pyrrolidinyl)-thio]-1-oxopropyl]-L-proline.

7. The compound in accordance with claim 1, 1-[3-[(1-ethyl-2,5-dioxo-3-pyrrolidinyl)-thio]-1-oxopropyl]-2-piperidinecarboxylic acid.

* * * * *

UNITED STATES PATENT AND TRADEMARK OFFICE
CERTIFICATE OF CORRECTION

PATENT NO. : 4,179,568
DATED : December 18, 1979
INVENTOR(S) : Allen I. Cohen, et al It is certified that error appears in the above-identified patent and that said Letters Patent are hereby corrected as shown below:

In column 4, line 16, the portion of the line reading "N 7.79" should read -- N 7.97--

In column 4, line 54, the elemental analysis should include a nitrogen analysis as follows: under "calc'd" add --N 8.76-- and under "found" add --8.52--

Signed and Sealed this

Twenty-third Day of September 1980

[SEAL]

Attest:

SIDNEY A. DIAMOND

Attesting Officer

Commissioner of Patents and Trademarks